US009643992B2

(12) United States Patent
Ren et al.

(10) Patent No.: US 9,643,992 B2
(45) Date of Patent: May 9, 2017

(54) TWO CRYSTAL FORMS OF GINSENOSIDE C-K AND METHOD FOR PREPARING SAME

(71) Applicant: Zhejiang Hisun Pharmaceutical Co., Ltd., Zhejiang (CN)

(72) Inventors: Guobin Ren, Shanghai (CN); Changliang Dai, Zhejiang (CN); Jinyao Chen, Shanghai (CN); Feng Chen, Zhejiang (CN); Minghui Qi, Shanghai (CN); Wenming Zhu, Zhejiang (CN); Minghuang Hong, Shanghai (CN); Hua Bai, Zhejiang (CN)

(73) Assignee: Zhejiang Hisun Pharmaceutical Co., Ltd., Zhejiang (CN)

( * ) Notice: Subject to any disclaimer, the term of this patent is extended or adjusted under 35 U.S.C. 154(b) by 137 days.

(21) Appl. No.: 14/389,345

(22) PCT Filed: Apr. 1, 2013

(86) PCT No.: PCT/CN2013/073562
§ 371 (c)(1),
(2) Date: Sep. 29, 2014

(87) PCT Pub. No.: WO2013/149571
PCT Pub. Date: Oct. 10, 2013

(65) Prior Publication Data
US 2015/0057440 A1 Feb. 26, 2015

(30) Foreign Application Priority Data
Apr. 1, 2012 (CN) .......................... 2012 1 0093293

(51) Int. Cl.
*C07J 17/00* (2006.01)
(52) U.S. Cl.
CPC ......... *C07J 17/005* (2013.01); *C07B 2200/13* (2013.01)
(58) Field of Classification Search
CPC ..................... C07J 17/005; C07B 2200/13
USPC ........................................................ 536/5
See application file for complete search history.

(56) References Cited

FOREIGN PATENT DOCUMENTS

| CN | 1417345 | A | | 5/2003 | |
| --- | --- | --- | --- | --- | --- |
| CN | 1465694 | A | | 1/2004 | |
| CN | 1570133 | A | | 1/2005 | |
| CN | 101139562 | A | | 3/2008 | |
| CN | 101921304 | | * | 12/2010 | .............. C07J 17/00 |
| CN | 102251009 | A | | 11/2011 | |
| CN | 101921304 | A | | 12/2012 | |
| CN | 103087138 | A | | 5/2013 | |
| JP | 2003519698 | A | | 6/2003 | |
| WO | WO 01/51919 | A2 | | 7/2001 | |

OTHER PUBLICATIONS

Li et al, Cryst. Res. Tech. 47 (4), 377-384, published online Jan. 31, 2012.*
Li et al, Cryst. Res. Tech., 2012, 47(4), 377-384.*
Partial European Search Report, dated Oct. 13, 2015, from corresponding or related European Patent Application No. 13772541.2.
Wei Zhou et al: "X-ray Structure Investigation of 20-O-B-D-glucopyranosyl-20(S)-protopanaxadiol," (2009) J Chem Crystallogr; vol. 39; pp. 99-103.
Zhou, Wei et al: "Method for purifying ginsenoside compound-k with macroporous resin" (2010) XP-002743475.
Ji-Eun Shin et al: "Cytotoxicity of Compound K (IH-901) and Ginsenoside $R_{h2}$, Main Biotransformants of Ginseng Saponins by Bifidobacteria, against Some Tumor Cells," (2003) J. Ginseng Res.; vol. 27; pp: 129-134.
Runyan Li et al: "Correlation of Solubility and Prediction of the Mixing Properties of Ginsenoside Compound K in Various Solvents," (2012) Industrial & Enginerring Chemistry Research; vol. 51; pp. 8141-8148.
Runyan Li et al: "Isolation, characterization and phase transformation of new ginsenoside compound k hydrate and methanol solvates," (2012) Cryst. Res. Technol.; vol. 4; pp: 377-384.
Im Kwang Sik et al: "A modified alkaline hydrolysis of total ginsenosides yielding genuine aglycons and prosapogenols," (1995) Arch. Pharm. Res.; vol. 18; pp. 454-457.
Gu Huike et al: "Molecular modeling of crystal morphology of ginsenoside compound K solvates and its crystal habit modification by solvent molecules," (2013) Journal of Crystal Growth; vol. 373; pp: 146-150.
Japanese Office Action, dated Nov. 10, 2015, from corresponding Japanese Patent Application No. 2015-502084.
Cui-Cui et al.: "Extraction of ginsenoside Compound-K," Journal of Dalian Polytechnic University 2009, v.28, pp. 87-89.
Kawaguchi et al.: "Drug and crystal polymorphism," Journal of human environmental engineering 2002, v.4, pp. 310-317.
"Setting new drugs on the specifications and test methods," Pharmaceutical trial departure No. 568, 2001, Pharm Stage 2007, vol. 6, No. 10, p. 48-53.
"API from screening and selection in drug discovery stage," Pharm Stage 2007, vol. 6, No. 10, p. 20-25.
Yamano: "Approach to Crystal Polymorph in Process Research of New Drug," Journal of Synthetic Organic Chemistry, Japan 2007,vol. 65, No. 9,p. 907-913.
Bryn et al.: "Pharmaceutical Solids: A Strategic Approach to Regulatory Considerations," Pharmaceutical Research 1995, v.12, pp. 945-954.
"Crystallization of Polymorphs and Pseudo-polymorphs and Its Control," Pharm Stage 2007, vol. 6, No. 10, p. 48-53.
International Search Report dated Jul. 11, 2013 from corresponding International Application No. PCT/CN2013/073562.
International Search Report dated Jul. 11, 2013 from potentially related International Application No. PCT/CN2013/073560.
Zhou, W., *Studies on the preparation, crystal structure and bioactivity of ginsenoside compound K*, Journal of Asian Natural Products Research, vol. 8, No. 6, Sep. 2006, 519-527.
Zhou, W, et al., *X-Ray Stucture Investigation of (20S)-20-O-β-D-glucopyranosyl-protopanaxadiol and antitumor effect on Lewis lung carcinoma in vivo.* Chemistry & Biodiversity, 2009, vol. 6, pp. 380-388.

(Continued)

*Primary Examiner* — Ganapathy Krishnan
(74) *Attorney, Agent, or Firm* — Wolf, Greenfield & Sacks, P.C.

(57) ABSTRACT

Provided are ginsenoside C-K polymorphic forms and a method for preparing same. The ginsenoside C-K polymorphic forms are crystal form D and crystal form H.

7 Claims, 4 Drawing Sheets

(56) References Cited

OTHER PUBLICATIONS

Zhou, W, *Studies on the preparation, crystal structure and bioactivity of ginsenoside compound K*, Chinese Doctoral Dissertations Full-text Database (Medicine and Health Sciences). No. 3, pp. 51-52, Feb. 10, 2009.

\* cited by examiner

TWO CRYSTAL FORMS OF GINSENOSIDE C-K AND METHOD FOR PREPARING SAME

CROSS REFERENCE TO RELATED APPLICATIONS

This application is the national phase of International Application No. PCT/CN2013/073562, filed on Apr. 1, 2013, which claims the benefit of priority to Chinese Patent Application No. 201210093293.3, filed with the Chinese State Intellectual Property Office on Apr. 1, 2012, which applications are incorporated herein by reference to the maximum extend allowable by law.

FIELD OF THE INVENTION

The present invention relates to the pharmaceutical field, and more particularly, the present invention relates to two novel crystal forms of ginsenoside C-K and the method for preparing the same.

BACKGROUND OF THE INVENTION

Ginsenosides are primary active ingredients of ginseng, in which ginsenoside C-K belongs to a diol-type ginsenoside, and is not present in natural ginseng. Ginsenoside C-K is the major degradation product of other diol-type ginsenosides in human intestinal tract, which is indeed the entity that is absorbed and effects in the human body. Ginsenoside C-K not only has favorable activities in the aspects including anti-tumor, anti-inflammation, anti-allergy, liver protection and the like, but also plays a good role in regulation of both nervous system and immune system.

At present, reference 1 (Studies on the preparation, crystal structure and bioactivity of ginsenoside compound K, *Journal of Asian Natural Products Research*, 2006, 8(6), 519-527) has reported a crystal form of ginsenoside C-K, which is designated as crystal form G. It has been reported that the crystal form is a dihydrate of ginsenoside C-K, which belongs to the monoclinic system and has the following cell parameters: a=15.992(3) Å, b=11.960(19) Å, c=20.127(3) Å, α=90°, β=101.85°, γ=90°, V=3767.5(11)Å$^3$, and Z=4, in which the solvent system used consists of acetonitrile and water.

Generally, for an active pharmaceutical ingredient, the bioavailability may vary due to different crystal forms. Furthermore, physicochemical properties, including stability, flowability and compressibility may also be different, which will have certain influence on its applications. The crystal form D and crystal form H of ginsenoside C-K provided in the present invention have better stability than the existing crystal form G.

SUMMARY OF THE INVENTION

In the present invention, two novel crystal forms including crystal form D and crystal form H of ginsenoside C-K are provided, and the methods for preparing the two crystal forms are also provided, in which the crystal form D is the crystal of ginsenoside C-K monohydrate.

In one aspect of the present invention, the crystal form D of ginsenoside C-K is provided, which is characterized in that there are diffraction peaks at 2θ values (°) of about 6.39, 12.71, 13.30, 15.79, 16.14, 16.44, 20.03, 20.74 and 24.29 in the XRPD pattern, and preferably, these peaks are major peaks, in which the error range of 2θ value is ±0.2.

In further embodiments, the crystal form D of ginsenoside C-K also has diffraction peaks at 2θ values (°) of about 10.66, 11.21, 16.85, 17.27, 19.05, 21.33, 21.65, 22.52, 23.48, 24.93, 25.46, 26.76, 27.99, 29.15, 30.39, and 34.14, and further preferably, these peaks are minor diffraction peaks, in which the error range of 2θ value is ±0.2.

In further embodiments, the crystal form D of ginsenoside C-K has diffraction peaks of the XRPD pattern substantially as shown in FIG. 1.

The specific data of the XRPD pattern are listed in the table below:

TABLE 1

The XRPD diffraction angles of the crystal form D of ginsenoside C-K

| No. | 2θ (°) | I % |
|---|---|---|
| 1 | 6.39 | 100 |
| 2 | 10.66 | 1 |
| 3 | 11.21 | 3.8 |
| 4 | 12.71 | 12.7 |
| 5 | 13.30 | 39.3 |
| 6 | 15.79 | 23.7 |
| 7 | 16.14 | 27.3 |
| 8 | 16.44 | 35.4 |
| 9 | 16.85 | 3.8 |
| 10 | 17.27 | 6.8 |
| 11 | 19.05 | 2 |
| 12 | 20.03 | 10.9 |
| 13 | 20.74 | 9.3 |
| 14 | 21.33 | 2.4 |
| 15 | 21.65 | 1.3 |
| 16 | 22.52 | 2.5 |
| 17 | 23.48 | 2.7 |
| 18 | 24.29 | 8.6 |
| 19 | 24.93 | 3 |
| 20 | 25.46 | 6.3 |
| 21 | 26.76 | 2 |
| 22 | 27.99 | 3.8 |
| 23 | 29.15 | 2.6 |
| 24 | 30.39 | 2 |
| 25 | 34.14 | 2.9 |

In further embodiments, the crystal form D of ginsenoside C-K has an endothermic peak at around 154±5° C. in the DSC pattern.

The crystal form D of ginsenoside C-K is characterized in that it is a ginsenoside C-K monohydrate, belongs to monoclinic system, and has the following cell parameters: a=15.856(3) Å, b=7.582(2) Å, c=16.567(3) Å, α=γ=90.00°, β=117.95 (3)°, cell volume V=1759.4(6) Å$^3$, and the number of asymmetric unit in the cell Z=2.

In another embodiment of the present invention, a method for preparing the crystal form D of ginsenoside C-K is provided, which comprises: (1) dissolving ginsenoside C-K in an organic solvent or a mixed solvent of organic solvent and water, preferably in a mixed solvent of organic solvent and water in a volume ratio of 3:1; (2) adding dropwise water, preferably the water in a volume of 1-4 folds of the organic solvent or the mixed solvent of organic solvent and water in step (1); (3) stirring, filtering, and drying the filter cake under vacuum to obtain the crystal form D of ginsenoside C-K. The organic solvent is selected from the group consisting of n-propanol and tetrahydrofuran.

In a further embodiment of the present invention, a method for preparing the crystal form D of ginsenoside C-K is additionally provided, which comprises: (1) dissolving ginsenoside C-K in a mixed solvent of acetonitrile and water, or a mixed solvent of dimethyl sulfoxide and nitromethane, (2) removing the solvent slowly by evaporation, or removing a portion of the solvent slowly by evaporation, followed by filtration; (3) drying the resultant solid under vacuum to obtain the crystal form D of ginsenoside C-K.

In the above embodiments of the method, the ginsenoside C-K used can be any form of ginsenoside C-K, including the crystal form G of ginsenoside C-K.

In another aspect of the present invention, a crystal form H of ginsenoside C-K is provided, which is characterized in that there are diffraction peaks at 2θ values (°) of about 5.53, 6.71, 11.11, 13.36, 14.64, 15.59, 15.97, 17.25, 18.18, 19.67, 20.76, 22.40, 23.80, 24.69, 26.60 and 28.22 in the XRPD pattern, and preferably, these peaks are major diffraction peaks, in which the error range of 2θ value is ±0.2.

In further embodiments, the crystal form H of ginsenoside C-K of the present invention also has diffraction peaks at 2θ values (°) of 11.82, 12.77, 14.23, 19.12, 20.47, 32.29 and 42.29, and preferably, these peaks are minor diffraction peaks, in which the error range of 2θ value is ±0.2.

In further embodiments, the crystal form H of ginsenoside C-K has the diffraction peaks of the XRPD pattern substantially as shown in FIG. 3.

The specific data of the XRPD pattern are listed in the table below:

TABLE 2

The XRPD diffraction angles of the crystal form H of ginsenoside C-K

| No. | 2θ (°) | I % |
|---|---|---|
| 1 | 5.53 | 69.1 |
| 2 | 6.71 | 100 |
| 3 | 11.11 | 34.2 |
| 4 | 11.82 | 7.5 |
| 5 | 12.77 | 19.1 |
| 6 | 13.36 | 45.9 |
| 7 | 14.23 | 6.6 |
| 8 | 14.64 | 67.7 |
| 9 | 15.59 | 76.8 |
| 10 | 15.97 | 63 |
| 11 | 17.25 | 23.5 |
| 12 | 18.18 | 13.8 |
| 13 | 19.12 | 5.1 |
| 14 | 19.67 | 13.3 |
| 15 | 20.47 | 11.3 |
| 16 | 20.76 | 30.8 |
| 17 | 22.40 | 15.5 |
| 18 | 23.80 | 18.9 |
| 19 | 24.69 | 10.5 |
| 20 | 26.60 | 10.6 |
| 21 | 28.22 | 13.1 |
| 22 | 32.29 | 6.4 |
| 23 | 42.29 | 5 |

In further embodiments, the crystal form H of ginsenoside C-K has an endothermic peak at 181±5° C. in the DSC pattern.

In another embodiment of the present invention, a method for preparing the crystal form H of ginsenoside C-K is provided, which comprises: (1) dissolving ginsenoside C-K in a mixed solvent of 1-methyl-2-pyrrolidone and butyl acetate, (2) removing a portion of the solvent slowly by evaporation at room temperature to obtain a suspension; (3) filtering, drying the resultant solid under vacuum to obtain the crystal form H of ginsenoside C-K.

In another embodiment of the present invention, a method for preparing the crystal form H of ginsenoside C-K is additionally provided, which comprises: (1) placing ginsenoside C-K in acetone, heating and stirring the resultant suspension, and most preferably heating to around 50° C.; (2) filtering, and drying the resultant filter cake under vacuum to obtain the crystal form H of ginsenoside C-K.

In another embodiment of the present invention, a method for preparing the crystal form H of ginsenoside C-K is additionally provided, which comprises: (1) dissolving ginsenoside C-K in an organic solvent at increased temperature; (2) cooling and standing to obtain a solid; (3) filtering, and drying the resultant solid to obtain the crystal form H of ginsenoside C-K, wherein the organic solvent is selected from the group consisting of acetone, butanone, ethyl acetate, butyl acetate and a combination thereof.

In the above embodiments of method, the ginsenoside C-K used can be any form of ginsenoside C-K, including the crystal form G.

The thermostability data of the crystal form D and crystal form H, together with crystal form G are also provided in the present invention, suggesting that the two novel crystal forms have better stability than crystal form G.

DETAILED DESCRIPTION OF THE INVENTION

The crystal form of all of the materials used in the examples is crystal form G (obtained according to reference 1 mentioned above).

1. Preparation of the Crystal Form D of Ginsenoside C-K

Example 1

1 g ginsenoside C-K was added into 60 ml mixed solvent of acetonitrile and water (in a volume ratio of 3:1), and dissolved by stirring. After filtration, the filtrate was placed at room temperature for 2 days, from which rod-like crystals were taken out and analyzed by SXRD. The results suggested that the crystal belonged to monoclinic system, and had the following cell parameters: a=15.856(3) Å, b=7.582(2) Å, c=16.567(3) Å, α=γ=90.00°, β=117.95 (3)°, cell volume V=1759.4(6) Å$^3$, and the number of asymmetric unit in the cell Z=2. The simulated XRPD pattern was shown in FIG. 3.

Example 2

Figure 4:
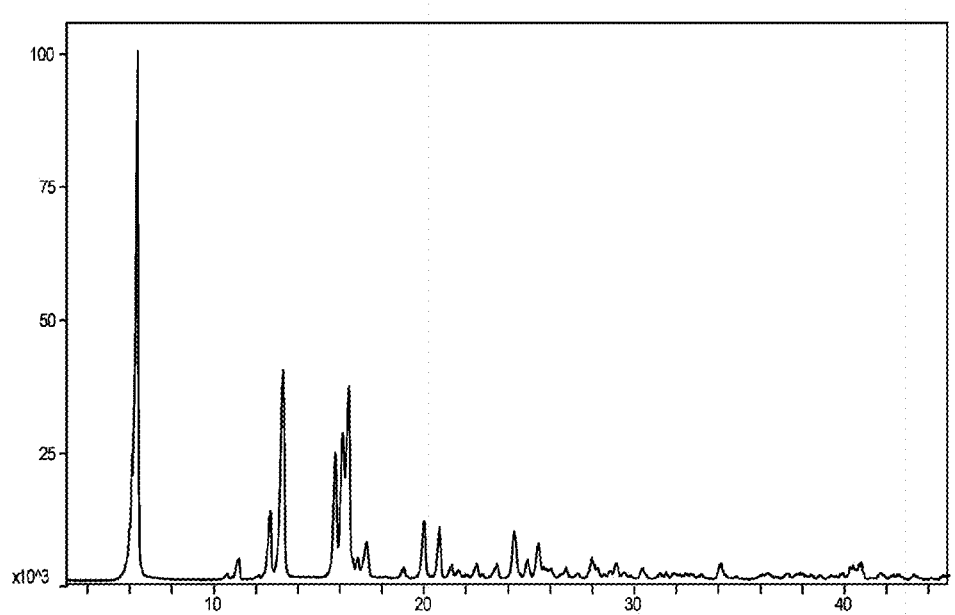
FIG. 4 is the X-ray powder diffraction pattern of the crystal form D product obtained in Example 2.
Figure 5:
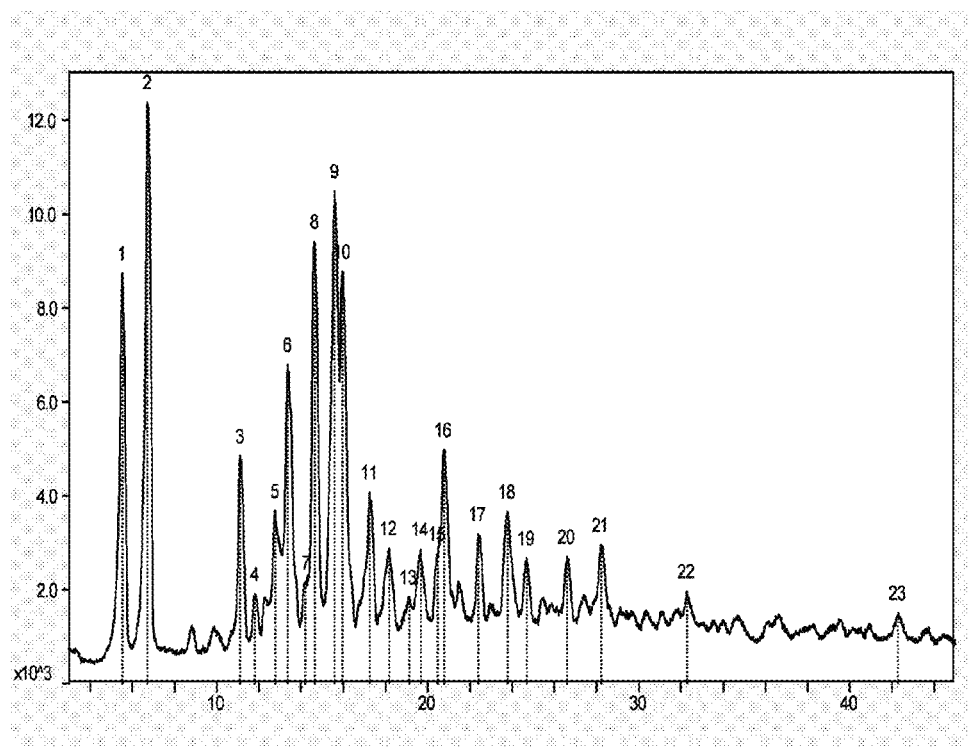
FIG. 5 is the X-ray powder diffraction pattern of the crystal form H of ginsenoside C-K obtained in Example 4, and the X-ray powder diffraction pattern of the crystal form H obtained in Example 5 is consistent with FIG. 5.
Figure 6:
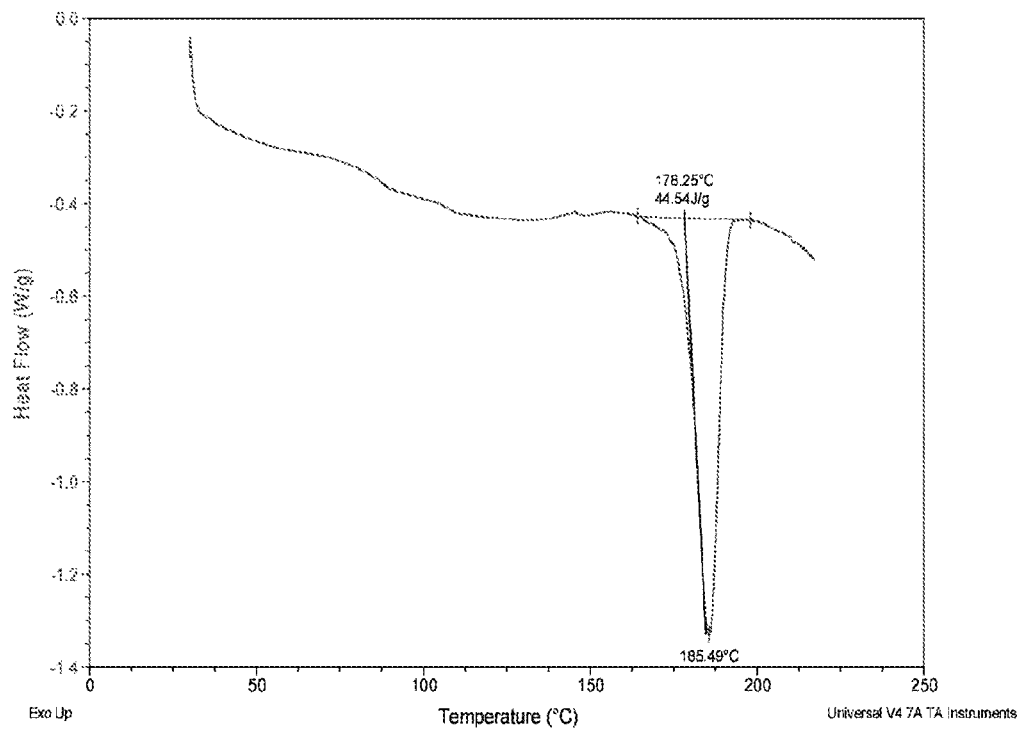
FIG. 6 is the DSC pattern of the crystal form H of ginsenoside C-K obtained in Example 4, and the DSC pattern of the crystal form H obtained in Example 5 is consistent with FIG. 6.

6 g ginsenoside C-K was placed in a container, into which 10 ml water and 30 ml n-propanol were added. After dissolution by stirring, 80 ml water was added dropwise. After filtration, the filter cake was washed twice using 40 ml water, dried at room temperature under vacuum to obtain the crystal form D of ginsenoside C-K. Its XRPD pattern was shown in FIG. 4.

Example 3

3 g ginsenoside C-K was placed in a container, into which 90 ml nitromethane and 10 ml dimethyl sulfoxide were added. After dissolution by stirring, a portion of the solvent was removed by evaporation slowly. After filtration, the filter cake was washed twice using 40 ml water, dried at room temperature under vacuum to obtain the crystal form D of ginsenoside C-K.

2. Preparation of the Crystal Form H of Ginsenoside C-K

Example 4

1 g ginsenoside C-K was placed in a container, into which 10 ml NMP was added followed by 60 ml butyl acetate. After dissolution, a portion of the solvent was removed by evaporation slowly to obtain the solid. After filtration, the solid was dried at room temperature under vacuum to obtain the crystal form H of ginsenoside C-K.

Example 5

2 g ginsenoside C-K was placed in a container, into which 20 ml acetone was added and warmed up to 50° C. to form a suspension. After stirring for 72 h, the suspension was filtered and the filter cake was dried under vacuum to obtain the crystal form H of ginsenoside C-K.

Example 6

Figure 7:
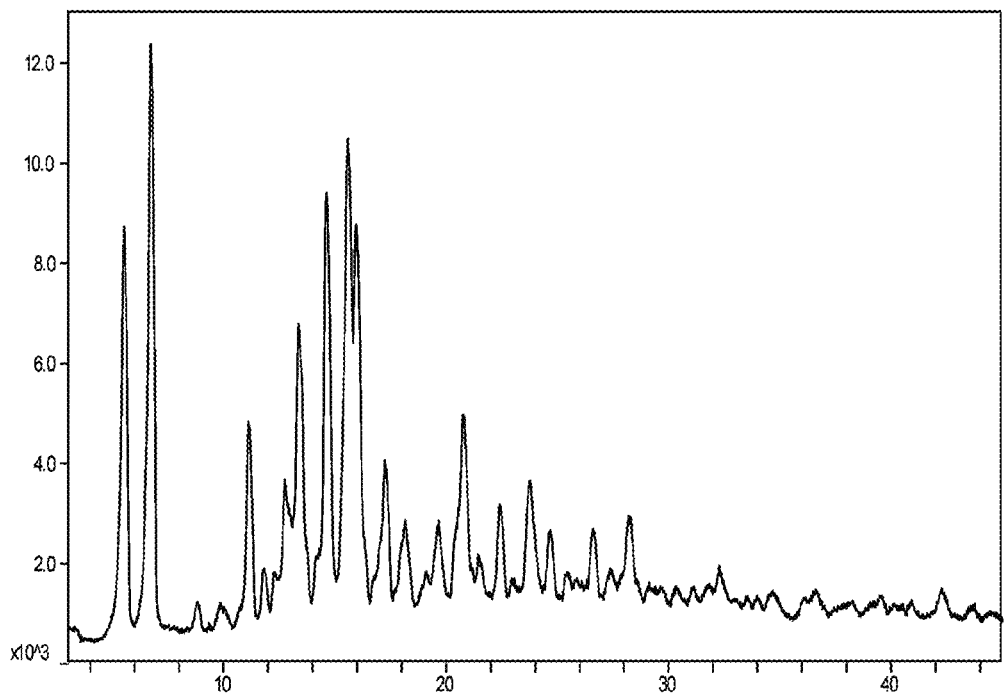
FIG. 7 is the X-ray powder diffraction pattern of the crystal form H obtained in Example 6.

2.3 g ginsenoside C-K was placed in a container, into which 100 ml acetone was added and warmed up to 55° C. After dissolution by stirring, the solution was cooled to room temperature and placed for 12 h to develop a solid. After filtration, the filter cake was dried under vacuum to obtain the crystal form H of ginsenoside C-K. Its XRPD pattern was shown in FIG. 7.

Example 7

0.7 g ginsenoside C-K was placed in a container, into which 15 ml ethyl acetate and 45 ml acetone were added and warmed up to 45° C. After dissolution by stirring, the solution was cooled to 4° C. to develop a solid. After filtration, the filter cake was dried under vacuum to obtain the crystal form H of ginsenoside C-K.

3. Thermostability Test

The samples of crystal form D, crystal form H and crystal form G were each placed for 1 week at 80° C., and subsequently the changes of the crystal form were detected. The results showed that under such conditions, no change was observed for the crystal form D and crystal form H, whereas the crystal form G changed to crystal form D, which indicated that both crystal form H and crystal form D had better thermostability.

TABLE 3

Results of the thermostability test

| The crystal form before test | Test temperature | Test duration | The crystal form after test |
|---|---|---|---|
| D | 80° C. | 1 week | D |
| H | 80° C. | 1 week | H |
| G | 80° C. | 1 week | D |

The invention claimed is:

1. A crystal form H of ginsenoside C-K, characterized in that there are diffraction peaks at 2θ values (°) of 5.53, 6.71, 11.11, 13.36, 14.64, 15.59, 15.97, 17.25, 18.18, 19.67, 20.76, 22.40, 23.80, 24.69, 26.60, and 28.22 in the XRPD pattern, wherein the error range of 2θ value is ±0.2.

2. The crystal form H according to claim 1, wherein said crystal form also has diffraction peaks at 2θ values (°) of 11.82, 12.77, 14.23, 19.12, 20.47, 32.29, and 42.29, wherein the error range of 2θ value is ±0.2.

Figure 1:
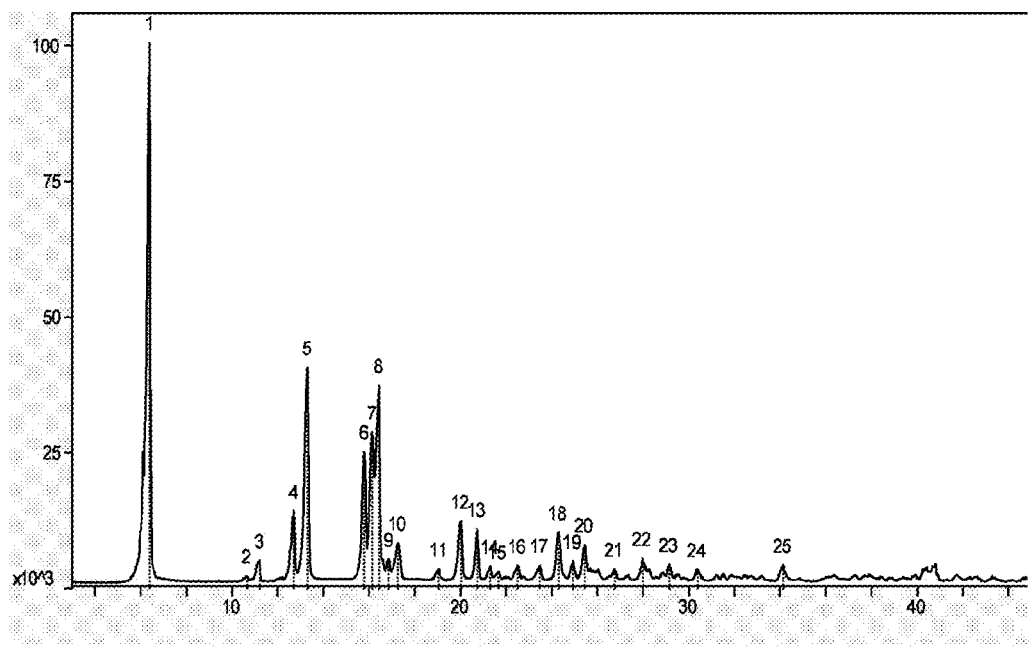
FIG. 1 is the X-ray powder diffraction pattern of the crystal form D of ginsenoside C-K obtained in Example 1.
Figure 2:
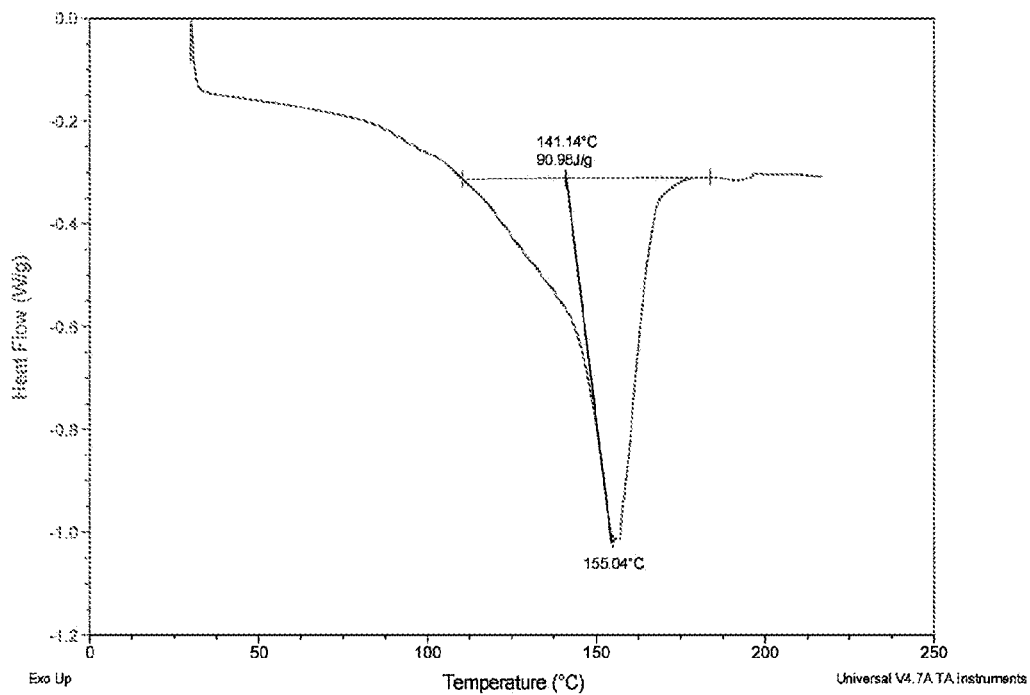
FIG. 2 is the DSC pattern of the crystal form D of ginsenoside C-K obtained in Example 1.
Figure 3:
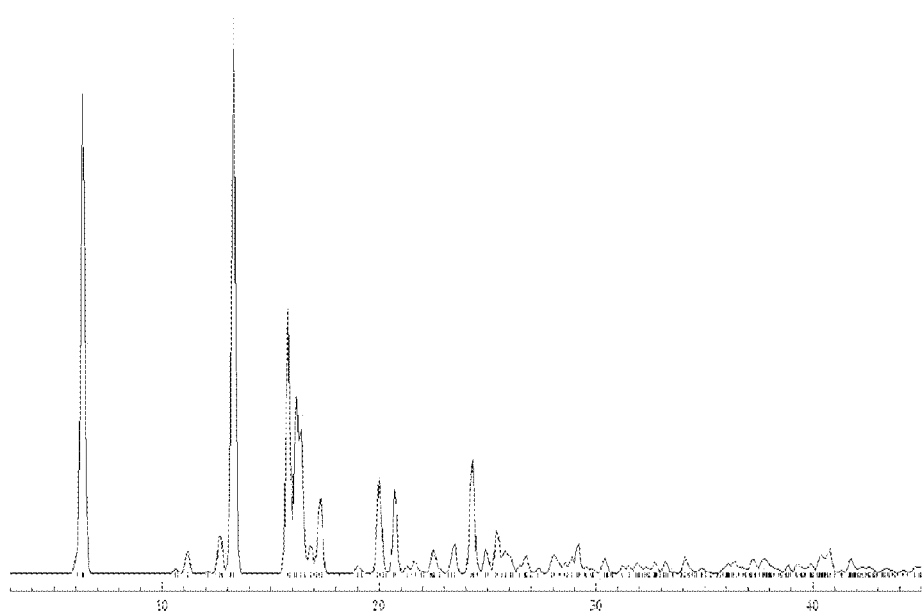
FIG. 3 is the simulated X-ray powder diffraction pattern of the crystal form D of ginsenoside C-K monocrystalline obtained in Example 1.

3. The crystal form H according to claim 1, wherein said crystal form has diffraction peaks of the XRPD pattern substantially as shown in FIG. 3.

4. The crystal form H according to claim 1, wherein said crystal form has an endothermic peak at 181±5° C. in the DSC pattern.

5. A method for preparing the crystal form H according to claim 1, comprising:
(1) dissolving ginsenoside C-K in a mixed solvent of 1-methyl-2-pyrrolidone and butyl acetate;
(2) removing a portion of the solvent slowly by evaporation at room temperature to obtain a suspension;
(3) filtering, drying solid under vacuum to obtain the crystal form H of ginsenoside C-K.

6. A method for preparing the crystal form H according to claim 1, comprising:
(1) placing ginsenoside C-K in acetone, heating and stirring the resultant suspension;
(2) filtering, and drying under vacuum to obtain the crystal form H of ginsenoside C-K.

7. A method for preparing the crystal form H according to claim 1, comprising:
(1) dissolving ginsenoside C-K in an organic solvent at above room temperature, wherein the organic solvent is selected from the group consisting of acetone, butanone, ethyl acetate, butyl acetate and a combination thereof;
(2) cooling and standing to obtain a solid;
(3) filtering, and drying the resultant solid to obtain the crystal form H of ginsenoside C-K.

* * * * *